United States Patent
Warek et al.

(10) Patent No.: US 10,226,064 B2
(45) Date of Patent: Mar. 12, 2019

(54) NITRITE-DEGRADING AND TSNA-DEGRADING BACTERIA AND METHODS OF MAKING AND USING

(71) Applicant: Altria Client Services LLC, Richmond, VA (US)

(72) Inventors: Ujwala Warek, Chester, VA (US); Mark T. Nielsen, Nicholasville, KY (US); Dongmei Xu, Glen Allen, VA (US); Mingwu Cui, Lexington, KY (US); Xue Luo, Richmond, VA (US); Xiaohong Jin, Glen Allen, VA (US); Elisabeth Miller, Chesterfield, VA (US); Kwang Choi, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 922 days.

(21) Appl. No.: 14/206,666

(22) Filed: Mar. 12, 2014

(65) Prior Publication Data
US 2014/0261481 A1    Sep. 18, 2014

Related U.S. Application Data

(60) Provisional application No. 61/794,854, filed on Mar. 15, 2013.

(51) Int. Cl.
| | | |
|---|---|---|
| C12N 1/20 | (2006.01) | |
| A24B 15/12 | (2006.01) | |
| A24B 15/24 | (2006.01) | |
| A24B 15/20 | (2006.01) | |

(52) U.S. Cl.
CPC ............ *A24B 15/245* (2013.01); *A24B 15/12* (2013.01); *A24B 15/20* (2013.01); *C12N 1/20* (2013.01)

(58) Field of Classification Search
None
See application file for complete search history.

(56) References Cited

U.S. PATENT DOCUMENTS

| | | | | |
|---|---|---|---|---|
| 3,847,163 A * | 11/1974 | Molyneux | ............... | A24B 15/24 131/297 |
| 4,528,993 A | 7/1985 | Sensabaugh et al. | | |
| 4,622,982 A | 11/1986 | Gaisch et al. | | |
| 4,660,577 A | 4/1987 | Sensabaugh et al. | | |
| 4,848,373 A | 7/1989 | Lenkey | | |
| 5,372,149 A | 12/1994 | Roth et al. | | |
| 6,756,221 B1 * | 6/2004 | Yamaguchi | ............... | A23J 3/34 426/56 |
| 2004/0118422 A1 | 6/2004 | Lundin et al. | | |
| 2005/0115576 A1 | 6/2005 | Koga et al. | | |
| 2005/0178398 A1 | 8/2005 | Breslin et al. | | |
| 2005/0244521 A1 | 11/2005 | Strickland et al. | | |
| 2006/0191548 A1 | 8/2006 | Strickland et al. | | |
| 2012/0024301 A1 | 2/2012 | Carroll et al. | | |
| 2012/0031414 A1 | 2/2012 | Atchley et al. | | |
| 2012/0031416 A1 | 2/2012 | Atchley et al. | | |

FOREIGN PATENT DOCUMENTS

| | | |
|---|---|---|
| CN | 1580237 | 2/2005 |
| EP | 2526787 | 11/2012 |

OTHER PUBLICATIONS

Vancanneyt et al., International Journal of Systematic Bacteriology, 1996, vol. 64 (4), p. 926-932.*
Sethunathan, N., Residue Rev. 47:143-165.*
https://archive.org/stream/modernamericant01unkngoog/modernamericant01unkngoog_djvu.txt, 1910, accessed May 9, 2017, one page.*
Burton et al., "Distribution of Tobacco Constituents in Tobacco Leaf Tissue. 1. Tobacco-Specific Nitrosamines, Nitrate, Nitrite, and Alkaloids," *J. Agric. Food Chem.*, 1992, 40:1050-1055.
Bush et al., "Formation of Tobacco-specific Nitrosamines in Air-cured Tobacco," *Recent Advances in Tobacco Science*, Symposium of the 55th Tobacco Science Research Conference, 2001, 27:23-46.
Tso, "Chapter 1: Seed to Smoke," *Tobacco, Production, Chemistry and Technology*, Davis & Nielsen, Eds., 1999, 33 pages.
International Search Report and Written Opinion in International Application No. PCT/US2014/024647, dated Sep. 16, 2014, 16 pages.
GenBank AB517709.1, Oct. 1, 2010, retrieved on Oct. 14, 2014, 1 page.
Hongying et al., "Identification and primary application of TSNA degrading bacterial strain AS97 isolated from aging tobacco leaves," College of Plant Protection, Shaanxi Key Laboratory of Molecular Biology for Agriculture, Oct. 2011, 51(10):1326-1333 (English Abstract Only).
International Preliminary Report on Patentability in International Application No. PCT/US2014/024647, dated Sep. 24, 2015, 10 pages.

* cited by examiner

*Primary Examiner* — Irene Marx

(57) ABSTRACT

Provided herein are bacterial strains that are capable of degrading nitrite and/or TSNAs. Also provided herein are methods of using such bacterial strains to degrade nitrite and/or TSNAs.

14 Claims, 10 Drawing Sheets
Specification includes a Sequence Listing.

Note: 70 ppm at Start

NITRITE-DEGRADING AND TSNA-DEGRADING BACTERIA AND METHODS OF MAKING AND USING

CROSS REFERENCE TO RELATED APPLICATIONS

This application claims the benefit of priority under 35 U.S.C. § 119(e) to U.S. Application No. 61/794,854 filed Mar. 15, 2013. The prior application is incorporated herein by reference in its entirety.

TECHNICAL FIELD

This disclosure generally relates to microbiology.

BACKGROUND

Tobacco-specific nitrosamines (TSNAs) are nitrosation products of secondary and tertiary alkaloid amines in tobacco. TSNAs are the result of a chemical reaction between tobacco alkaloids, such as nicotine and nornicotine, and unstable NOx radicals. It is generally understood that microbes on or in the tobacco plant before, during, or after curing are primarily responsible for the formation of nitrite, the predominant NOx precursor in the formation of TSNAs (Bush et al. *Recent Advances in Tobacco Science*. 27:23-46 (2001)).

A number of bacterial strains are described herein that degrade a number of different nitrite and/or TSNA species.

SUMMARY

This disclosure describes bacterial strains that are capable of degrading nitrite and/or TSNAs. This disclosure also describes methods of using such bacterial strains to degrade nitrite and/or TSNAs.

In one aspect, an isolated bacterial strain belonging to the genus *Myroides* is provided. Such a bacterial strain includes the 16S rDNA sequence shown in SEQ ID NO:1 or a 16S rDNA sequence having at least 99% sequence identity to SEQ ID NO:1, and exhibits efficient nitrite-degrading activity.

In another aspect, a method of reducing the amount of nitrites in strong extract liquor (SEL) is provided. Such a method typically includes contacting SEL with the isolated bacterial strain described above under conditions in which the amount of nitrite is reduced in the SEL, thereby producing a reduced-nitrite SEL. In one embodiment, the amount of nitrite in the tobacco is reduced by at least 50%.

Also provided is reduced-nitrite strong extract liquor (SEL) made by such a method, as well as reconstituted leaf comprising such reduced-nitrite SEL, wherein the reconstituted leaf is a reduced-nitrite reconstituted leaf.

In one aspect, an isolated bacterial strain belonging to the genus *Microbacterium* is provided. Such a bacterial strain exhibits efficient TSNA-degrading activity. In another aspect, a method of reducing the amount of one or more TSNAs in tobacco is provided. Such a method typically includes contacting the tobacco with the isolated bacterial strain described above under conditions in which the amount of one or more TSNAs is reduced in the tobacco. In one embodiment, the tobacco consists essentially of tobacco stems.

In one aspect, a composition comprising bacteria belonging to the genus *Sphingomonas* and bacteria belonging to the genus *Pseudomonas* is provided. Such a composition exhibits its efficient NNK-degrading activity. In another aspect, a method of reducing the amount of NNK in tobacco is provided. Such a method typically includes contacting the tobacco with the isolated bacterial strain described above under conditions in which the amount of NNK is reduced in the tobacco.

Also provided is tobacco made by any of the methods described above and a tobacco product that includes such tobacco. Representative tobacco products include, without limitation, a smokeless tobacco product and a combustible tobacco product.

In still another aspect, a method of screening a bacterial strain for the ability to degrade nitrite and/or one or more TSNAs is provided. Such a method typically includes a) inoculating a culture medium with a candidate bacterial strain in the presence of nitrite and/or one or more TSNAs; b) culturing the inoculated medium under appropriate conditions; and c) determining (i) bacterial growth relative to a control culture and/or (ii) the level of nitrite and/or one or more TSNAs relative to a control culture.

In some embodiments, the medium includes tobacco extract and/or tobacco debris. In some embodiments, the candidate bacterial strain is comprised on or within tobacco material. In some embodiments, bacterial growth is determined using optical density and the amount of nitrite and/or one or more TSNAs are determined using chromatography. Representative TSNAs are selected from the group consisting of N'-nitrosonornicotine (NNN), 4-(methylnitrosoamino)-1-(3-pyridyl)-1-butanone (NNK), N'-nitrosoanatabine (NAT), N'-nitrosoanabasine (NAB), and 4-(methylnitrosoamino)-1-(3-pyridyl)-1-butanal (NNAL). In some embodiments, such a method further includes identifying the genus to which the bacterial strain belongs. Representative methods of performing the identifying step includes 16s rDNA sequencing.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 4 are graphs showing the degradation of NO2- in scaled-up experiments.

Like reference symbols in the various drawings indicate like elements.

DETAILED DESCRIPTION

Figure 1A:
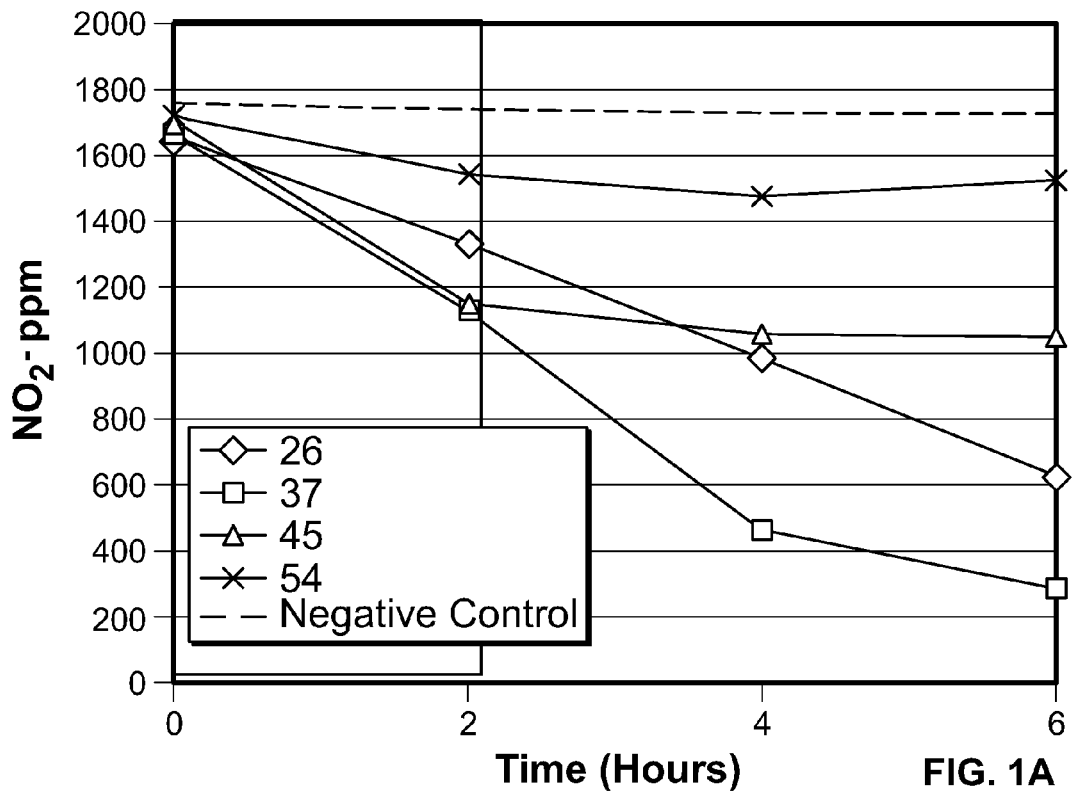
FIG. 1 are graphs showing the specific activity of M20 in sterile SEL (FIG. 1A) or native SEL (FIG. 1B).

TSNA are produced during curing and are formed by the reaction between alkaloids and nitrite-derived nitrosating species such as NO2, N2O3 and N2O4. Nitrite may accumulate as a result of nitrate reduction by bacteria, and TSNAs are formed by chemical reactions between nitrite (source of nitrosating species) and alkaloids. TSNAs are known in the art and include, for example, N'-nitrosonornicotine (NNN), 4-(methylnitrosoamino)-1-(3-pyridyl)-1-butanone (NNK), N'-nitrosoanatabine (NAT), N'-nitrosoanabasine (NAB), and 4-(methylnitrosoamino)-1-(3-pyridyl)-1-butanal (NNAL). Methods are described herein for identifying and characterizing bacteria that are able to degrade nitrite and/or TSNAs. In addition, methods are described herein for using bacteria to reduce nitrite and/or TSNAs in a number of tobacco-related products.

Methods of Screening for Nitrite- and/or TSNA-Reducing Bacteria

This disclosure describes a method of screening for bacteria that have the ability to degrade nitrite and/or one or more TSNAs. Bacteria that can be screened for the desired activity can be obtained from any source. For example, a variety of bacterial microorganisms can be obtained from any number of collections around the world (e.g., American Type Culture Collection (ATCC; Manassas, Va., USA); Microbial Culture Collection (Pune, India)) and screened for the desired characteristics. In addition, bacterial organisms residing on or within plant material (e.g., tobacco material) can be screened for the desired characteristics.

One or more candidate bacterial strains (e.g., from a collection, from tobacco material) are inoculated into culture medium. Conditions under which microorganisms are cultured are well known and routinely used in the art, and can include, for example, a temperature between 25 C and 45 C and shaking at about 50 RPM to about 240 RPM. For purposes of the methods herein, the culture medium should contain nitrite and/or one or more TSNAs. Nitrite and/or one or more TSNAs can be found naturally in the media, they can be added exogenously, or a combination thereof. Nitrite and/or one or more TSNAs can be added to the media directly (e.g., Sigma-Aldrich Chemical Co., St. Louis, Mo.), and/or via tobacco material (e.g., tobacco extract, tobacco dust or debris, tobacco stems).

Bacterial growth can be determined and monitored using methods that are well known to those skilled in the art. For example, one of the most common is a turbidity measurement, which relies upon the optical density (OD) of bacteria in suspension and uses a spectrophotometer. In addition, physical measurements (e.g., dry weight of cells following centrifugation) or chemical measurements (e.g., rate of oxygen consumption, nitrogen, protein or DNA content) can be used to determine and/or monitor bacterial growth in a culture. Obviously, plating to determine colony forming units (CFUs) also is a standard method for determining and/or monitoring bacterial growth in a culture.

The amount of nitrite and/or one or more TSNAs in a culture can be determined (e.g., measured) using, for example, chromatography methods (e.g., gas chromatography/thermal energy analysis (GC/TEA), liquid chromatography/mass spectrometry (LC/MS), and ion chromatography (IC)). In some instances, the amount of nitrite and/or one or more TSNAs present in the culture can be determined over time (e.g., at various time points). Additionally or alternatively, nitrite and/or one or more TSNAs can be determined in a culture and compared to a "control" culture (e.g., a culture lacking the candidate bacterial strain).

Once it has been determined that a candidate bacterial strain has the ability to degrade nitrite and/or one or more TSNAs, a number of methods can be used to identify the genus and/or species to which the bacterial strain belongs. For example, differential culturing methods (e.g., use of different media, use of different carbon sources) can be used to identify or eliminate various genus and/or species. Additionally or alternatively, molecular techniques such as, without limitation, 16s rDNA sequencing or RFLP analysis can be used to identify the genus and/or species of the bacterial strain.

As an alternative to screening for a bacterial strain that possesses the desired activity (i.e., nitrite- and/or TSNA-degrading activity), one or more bacterial strains can be conditioned (e.g., selectively conditioned) to degrade nitrite and/or one or more TSNAs. For example, one or more bacterial strains can be cultured in medium that contains, initially, a low amount of nitrite and/or TSNA (e.g., about 10 ppm up to about 50 ppm in total) and also contains at least one other carbon and/or nitrogen source. As the bacterial strains are serially cultured, the amount of nitrite and/or TSNA is progressively increased (e.g., up to about 100 ppm-500 ppm in total) while the other carbon and/or nitrogen sources are progressively reduced until, eventually, the nitrite and/or TSNA is the sole carbon and nitrogen source in the culture. This eliminates bacterial strains that are sensitive to nitrite and/or TSNA, and ultimately results in the selection of bacterial strains that are able to metabolize (i.e., degrade) nitrite and/or TSNA.

Nitrite- and/or TSNA-Degrading Bacteria

Using the methods described herein, several different bacterial strains were identified that possess the ability to degrade nitrites and/or TSNAs. One of the bacterial strains, designated M20, was identified based on its ability to efficiently degrade nitrites. The 16S rDNA sequence from M20 was obtained and, based on that sequence, M20 was determined to belong to the genus, *Myroides*. Twenty-five vials of the bacterial strain *Myroides odoratus* M20 were deposited with American Type Culture Collection under ATCC® Patent Deposit Designation PTA-125147. Based on experimental evidence, it was determined that the M20 bacteria prefers a pH of 7, has optimum activity at 26° C. to 37° C., is able to be inoculated at a high CFU/ml, can survive agitation of up to about 225 RPM, and exhibits maximum activity between 20 minutes and 2 hours.

The rDNA sequence of M20 was determined and is shown in SEQ ID NO:1. It would be appreciated that M20 bacterial strains having rDNA sequences with at least 98% sequence identity or at least 99% sequence identity to SEQ ID NO:1 also are provided. To calculate the percent sequence identity of two sequences, the first and second sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align differently with other sequences and hence, can have different percent sequence identity values over each aligned region. Two sequences can be aligned to determine percent sequence identity using the algorithm described by Altschul et al. (1997, *Nucleic Acids Res.*, 25:3389-3402), which is incorporated into BLAST (basic local alignment search tool) programs available at ncbi.nlm.nih.gov on the World Wide Web.

Another bacterial strain, designated M21, was identified based on its ability to efficiently degrade TSNAs. Based on microbial characterization techniques and preliminary results of molecular sequencing, the M21 bacterial strain was determined to belong to the *Microbacterium* genus. A third bacterial composition, designated M30, was identified based on its ability to efficiently degrade NNK. Based on microbial characterization techniques and preliminary results of molecular sequencing, the M30 bacterial composition was determined to be a bacteria belonging to the genus *Pseudomonas*.

The M20 and M21 bacterial strains were isolated, as were the bacterial strains within the M30 bacterial composition. "Isolated," with respect to bacteria, generally refers to a population (e.g., a culture) in which at least about 70% (e.g., about 75%, 80%, 85%, 90%, 95%, 99% or 100%) of the bacteria are the nitrite- and/or TSNA-degrading bacteria described herein. When referring to a bacterial strain, "isolated" refers to a population (e.g., a culture) in which at least about 70% (e.g., about 75%, 80%, 85%, 90%, 95%, 99% or 100%) of the bacteria is a genetically-identical bacterial strain.

The bacteria described herein can be provided in a composition. In addition to bacteria, a composition also can include media, buffers, one or more nutrients, one or more minerals, one or more co-factors, or any other component that is necessary to maintain viability of the bacteria. Additionally, components that are not related to the viability of the bacteria may be desirable in a composition such as, without limitation, a dye or color marker. In addition, methods of storing bacteria are known in the art, and typically include protecting the bacteria with a glycerol-based media and storage at very low temperatures (e.g., −80 C).

Methods of Using Nitrite- and/or TSNA-Reducing Bacteria
  A) In Reconstituted Leaf Reconstituted leaf is a sheet-like material made from tobacco by-products (e.g., recycled tobacco fines, tobacco stems, tobacco particles (e.g., particles less than 30 mesh in size)). Reconstituted leaf is made be extracting the soluble chemicals in the tobacco by-products, processing the remaining tobacco fibers into a paper-like sheet, and reapplying the extracted soluble chemicals in concentrated form into the paper-like sheet. The initial extract is typically referred to as strong extract liquor (SEL), while the concentrated form is referred to as concentrated extract liquor (CEL).

During production, the SEL typically is held in a SEL tank for about 4 hours or less at temperatures that range from 51 C to 77 C. Conditions in a typical SEL tank include, without limitation, a starting pH of 5.4 and a temperature that ranges from about 51 C to about 76 C. A typical SEL tank contains about $10^3$ CFU/ml to about $10^4$ CFU/ml natural microflora, and can have a nitrite content that ranges from about 5 ppm up to about 130 ppm. During processing, a SEL tank is typically agitated at about 60 RPM to about 75 RPM (e.g., about 65 RPM to about 70 RPM, about 67 RPM). The SEL then is processed through evaporators to produce the CEL, which is held in a CEL tank for 0 to 3 hours at temperatures that can range from 70 F to 120 F (e.g., 70 F to 80 F, 90 F to 100 F, 110 F to 120 F). Crystallizing the CEL produces a Denitrified Extract Liquor (DNCEL), which is stored in a DNCEL tank for no more than 48 hours (e.g., from 0 hours up to 48 hours) at temperatures of 40 F to 50 F. The DNCEL is then poured onto the tobacco fibers to ultimately form the reconstituted leaf.

The M20 bacterial strain described herein has been shown to be effective in reducing nitrites in SEL. While the rate of nitrite degradation by M20 will depend on the volume of SEL and the number of bacteria that are inoculated into the SEL, the data presented herein would indicated that the M20 bacterial strain can degrade at least 50% of the nitrite (e.g., at least 55%, 60%, 65%, 70%, 75%, 80%, 85%, 90%, 95%, 99% or 100% of the nitrite) within 24 hours (e.g., within 20 hours, 18 hours, 16 hours, 14 hours, 12 hours, 10 hours, 8 hours, 6 hours, 4 hours, 2 hours, 1 hour, or less than 1 hour). For example, it is a characteristic of M20 that, in 300 ml SEL (pH 7) at a temperature of 45 C with shaking at 225 RPM, M20, inoculated at a ratio of 1:1 into the SEL, degraded greater than 99% (e.g., essentially 100%) of the nitrite within 20 minutes after inoculation. See FIG. 4A.

The M20 bacterial strain, therefore, can be used to reduce the level of nitrite in SEL. The resulting reduced-nitrite SEL then can be used in the process of making reconstituted leaf. The reduced-nitrite reconstituted leaf can be used in combustible smoking products, resulting in reduced-nitrite combustible smoking products.

B) In Tobacco and Tobacco Products

The tobacco material treated with a nitrite- and/or TSNA-degrading bacterial strain can be freshly harvested (green) tobacco or the tobacco material can be cured, fermented, conditioned, or any combination thereof. For example, after harvesting, tobacco typically is cured using conventional means, e.g., air curing, fire curing, barn curing, sun curing. See, for example, Tso (1999, Chapter I in Tobacco, Production, Chemistry and Technology, Davis & Nielsen, Eds., Blackwell Publishing, Oxford). Optionally, cured tobacco then can be conditioned and/or fermented. Conditioning includes, for example, a heating, sweating or pasteurization step as described in U.S. Publication Nos. 2004/0118422 or 2005/0178398. Fermenting typically is characterized by high initial moisture content, heat generation, and a 10 to 20% loss of dry weight. See, for example, U.S. Pat. Nos. 4,528,993; 4,660,577; 4,848,373; and 5,372,149. Cured or cured and fermented tobacco then can be further processed (e.g., cut, expanded, blended, milled or comminuted) for use in any number of tobacco products.

The entire tobacco plant or any portion thereof can be contacted with a nitrite- and/or TSNA-degrading bacterial strain. For example, in dark tobacco, TSNA concentration is highest near the base and center of the leaf, particularly along the midvein of the leaf (referred to herein as the "stem"). See, for example, Burton et al. (J. Agric. Food Chem., 40:1050-5 (1992)); in dark tobacco, the stem can account for about 30% of the dry weight of a leaf, but can contain up to 75% of the total TSNAs in the leaf. Therefore, in certain instances, the tobacco stems can be separated from other tobacco parts (e.g., the lamina) by any method including, without limitation, by hand, and contacted with a nitrite- and/or TSNA-degrading bacterial strain as described herein. For example, tobacco material that contains at least 50% w/w stems (e.g., 60%, 70%, 80%, 90%, 95%, 99% or 100%) can be contacted with a nitrite- and/or TSNA-degrading bacterial strain.

One or more nitrite- and/or TSNA-degrading bacterial strains can be applied to tobacco material as an aqueous solution or in a dry form (e.g., lyophilized). Any suitable method, such as mixing or spraying can be used to apply an aqueous solution including one or more nitrite- and/or TSNA-degrading bacterial strains onto tobacco. One or more nitrite- and/or TSNA-degrading bacterial strains can be applied to a particular part of the tobacco (e.g., to stems that have been separated from other tobacco parts), or one or more nitrite- and/or TSNA-degrading bacterial strains can be applied to tobacco leaves (e.g., primed leaves, stalk cut leaves, or stalk-cut leaves attached to the tobacco stalk) or to the entire tobacco plant.

Irrespective of how the one or more nitrite- and/or TSNA-degrading bacterial strains are applied to the tobacco, the conditions under which nitrite and/or TSNAs are reduced can be adjusted to favor the ability of any given bacterial strain or combination of strains to degrade nitrite and/or TSNAs. Suitable conditions generally include maintaining the tobacco or tobacco product and the nitrite- and/or TSNA-degrading bacterial strain(s) at a moisture content of from about 45% to about 75% by weight (e.g., about 50% to about 70%, about 55% to about 65%, about 60%) and a temperature of from about 20° C. to about 45° C. (e.g., about 20° C., about 25° C., about 30° C., about 32° C., about 35° C., about 37° C., about 40 C, about 42 C, or about 45 C). In addition, suitable conditions also can include a pH of about 5 to about 8 (e.g., about 6 to about 8, about 6.5 to about 7.5, about 6.5 to about 8, or about 7).

The tobacco and the at least one nitrite- and/or TSNA-degrading bacterial strains can be incubated together in, for example, a rotating drum, which can be rotated or tumbled, for example, to provide aeration. It would be understood by those skilled in the art that additional components (e.g., buffers, salts, minerals, or other ingredients present) can be added to the tobacco and nitrite- and/or TSNA-degrading bacteria mixture to affect the rate and/or degree at which one or more nitrites and/or TSNAs are degraded.

The amount of nitrite and/or TSNA is considered to be reduced when the reduction in the amount of nitrite and/or TSNAs is statistically significant when compared to the amount of nitrite and/or TSNAs in corresponding control tobacco. As used herein, "corresponding control tobacco" refers to the same portion (e.g., stem, lamina or entire leaf) of the same tobacco variety, which was grown, harvested and otherwise treated (e.g., cured, or fermented) in the same manner as the tobacco contacted with the nitrite- and/or TSNA-reducing bacteria. A "statistically significant" reduction in nitrite and/or TSNAs refers to a p-value of less than 0.10, e.g., a p-value of less than 0.05, a p-value of less than 0.025 or a p-value of less than 0.01, using an appropriate parametric or non-parametric statistic, e.g., Chi-square test, Student's t-test, Mann-Whitney test, or F-test.

Using the methods described herein, nitrite and/or TSNA content in tobacco or a tobacco-related product can be reduced by about 40% to about 99% (e.g., by about 40% to about 50%, by about 40% to about 60%, by about 40% to about 70%, by about 40% to about 80%, by about 45% to about 60%, by about 45% to about 70%, by about 45% to about 90%, by about 50% to about 65%, by about 50% to about 75%, by about 50% to about 95%, by about 60% to about 75%, by about 60% to about 95%, by about 75% to about 95%, by about 75% to about 99%, by about 80% to about 95%, by about 90% to about 99%, or by about 95% to about 99%). In some cases, nitrite and/or TSNAs can be reduced to undetectable levels.

Reduced-nitrite and/or -TSNA tobacco can be used alone or blended with non-reduced-nitrite and/or -TSNA tobacco. As used herein, blends refer to combinations of tobaccos that have 1%-99% of one or more of the reduced-nitrite and/or -TSNA tobaccos described herein (e.g., 1%-10%, 5%-20%, 10%-25%, 15%-30%, 20%-40%, 25%-45%, 30%-50%, 40%-55%, 50%-60%, 55%-65%, 60%-70%, 75%-85%, 80%-85%, 80%-90%, 85%-95%, 90%-99%, or 95%-99% of the reduced-nitrite and/or -TSNA tobaccos described herein). The reduced-nitrite and/or -TSNA tobacco can be from the same variety or a different variety of tobacco than that of the control tobacco.

In some embodiments, reduced-nitrite and/or -TSNA tobacco can be conditioned and/or fermented. Conditioning includes, for example, a heating, sweating or pasteurization step as described in US 2004/0118422 or US 2005/0178398. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. Cured, or cured and fermented, reduced-nitrite and/or -TSNA tobacco as described herein also can be further processed (e.g., cut, expanded, blended, milled or comminuted).

Reduced-nitrite and/or -TSNA tobacco or a blend of tobacco that includes such reduced-nitrite and/or -TSNA tobacco can be used in any number of adult-consumer tobacco products. Without limitation, adult-consumer tobacco products include smokeless tobacco products, cigarette products, cigar products, loose tobacco, and tobacco-derived nicotine products. Representative smokeless tobacco products include, for example, chewing tobacco, snus, pouches, films, tablets, sticks, rods, and the like. See, for example, US 2005/0244521, US 2006/0191548, US 2012/0024301, US 2012/0031414, and US 2012/0031416 for examples of tobacco products.

In addition to tobacco treated with a nitrite- and/or TSNA-degrading bacterial strain, adult-consumer tobacco products described herein can include other ingredients such as binders, plasticizers, stabilizers, and/or flavorings. For example, edible films typically include ingredients that are known in the art including, without limitation, film forming agents, surfactants, plasticizers, flavoring agents, fillers, colorants, emulsifiers, binding agents, fragrances, lubricants, or preservatives. It will be appreciated that the ingredients can be adjusted to achieve the desired properties of the product. For example, the amount of a plasticizer can be adjusted to modify the brittleness of the product, or a filler can be added to modify the texture of the product.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Screening for Nitrite- and/or TSNA-Reducing Bacteria

Cured tobacco leaves or soil containing tobacco debris were added to culture media and cultured under standard conditions (e.g., 37 C, 180 RPM). Isolates that thrived in the culture were purified via single colony isolation and characterized further.

As described below, the bacterial strains obtained from the screenings were characterized for rate and extent of nitrite and/or TSNA degradation in a culture environment, and those isolates that exhibited degradation activity were identified using existing molecular techniques.

Example 2—Characterization of Nitrite- and/or TSNA-Reducing Bacteria

A primary culture of 20 ml of TSG media (i.e., TSB media+glucose) and 20 ml of filter-sterilized SEL was inoculated with the bacterial strain and cultured at 28 C while shaking at 225 rpm.

A full culture of TSG was prepared and inoculated with the primary culture above. About 200 ml of SEL (pH 7.0) was filter sterilized, spiked with NNN and NNK to a final concentration of 25 ppm, and added to the TSG media. The OD of the culture was immediately determined to obtain a 0 hr reading, and a 0 hr sample was plated on TSB media.

Samples were taken at 6 to 7 hrs after inoculation, at 1 day after inoculation, and at 2 days after inoculation. The amount of nitrite, nitrate, and TSNAs in the media was measured (in triplicate). At each time point, a sample also was plated on TSB media.

Example 3—Bacterial Isolates

Three bacterial isolates were identified that had nitrite and/or TSNA-degrading activity. The first strain, designated M20, was identified as having nitrite-degrading activity. Sequence analysis of the 16S rDNA determined that M20 was a member of the genus, *Myroides*. The sequence of the 16s rDNA is shown in SEQ ID NO:1.

```
                                           (SEQ ID NO: 1)
AGAGTTTGATCCTGGCTCAGGATGAACGCTAGCGGCAGGCCTAACACATG

CAAGTCGAGGGGTATAGAGAGCTTGCTTTCTAGAGACCGGCGGATGGGTG

AGTAACGCGTATGCAACCTACCTTTTACAGGGGAATAGCCCGGAGAAATT

CGGATTAATGCTCCATGGTTTATATGAATGGCATCATTTATATAATAAAG

ATTTATCGGTAAAAGATGGGCATGCGTATCATTAGCTAGTTGGTGTGGTA

ACGGCATACCAAGGCGACGATGATTAGGGGTCCTGAGAGGGAGATCCCCC

ACACTGGTACTGAGACACGGACCAGACTCCTACGGGAGGCAGCAGTGAGG

AATATTGGTCAATGGAGGCAACTCTGAACCAGCCATGCCGCGTGCAGGAT

GACGGTCCTATGGATTGTAAACTGCTTTTGTACGGGAAGAAATGTAATTA

CGTGTAATTATTTGACGGTACCGTAAGAATAAGGATCGGCTAACTCCGTG

CCAGCAGCCGCGGTAATACGGAGGATCCGAGCGTTATCCGGAATTATTGG

GTTTAAAGGGTTCGTAGGCGGTTTAGTAAGTCAGTGGTGAAATCTTATAG

CTTAACTATAAAATTGCCGTTGATACTGCTAGACTTGAATAGTATGGAAG

TAATTAGAATATGTAGTGTAGCGGTGAAATGCTTAGATATTACATGGAAT

ACCAATTGCGAAGGCAGATTACTACGTACTTATTGACGCTGATGAACGAA

AGCGTGGGTAGCGAACAGGATTAGATACCCTGGTAGTCCACGCCGTAAAC

GATGGATACTAGCTGTTCGGTTTTCGGACTGAGTGGCTAAGCGAAAGTGA

TAAGTATCCACCTGGGGAGTACGTTCGCAAGAATGAAACTCAAAGGAATT

GACGGGGGCCCGCACAAGCGGTGGAGCATGTGGTTTAATTCGATGATACG

CGAGGAACCTTACCAAGGCTTAAATGTAGATTGACAGGTTTAGAGATAGA

CTTTTCTTCGGACAATTTACAAGGTGCTGCATGGTTGTCGTCAGCTCGTG

CCGTGAGGTGTCAGGTTAAGTCCTATAACGAGCGCAACCCCTATTGTTAG

TTGCCAGCGGGTCATGCCGGGAACTCTAACAAGACTGCCGGTGCAAACCG

TGAGGAAGGTGGGGATGACGTCAAATCATCACGGCCCTTACGTCTTGGGC

TACACACGTGCTACAATGGCCAGTACAGAAAGCAGCTACCAGGCAACTGG

ATGCGAATCTCAAAAACTGGTCTCAGTTCGGATTGGAGTCTGCAACTCGA

CTCCATGAAGCTGGAATCGCTAGTAATCGGATATCAGCCATGATCCGGTG

AATACGTTCCCGGGCCTTGTACACACCGCCCGTCAAGCCATGGAAGCTGG

GGGTACCTGAAGTCGGTCGCCGCAAGGAGCTGCCTAGGGTAAAACTGGTA

ACTAGGGCTAAGTCGTAACAAGGTAGCCGTA
```

The second strain, designated M21, was identified as a TSNA-degrading microorganism. Sequencing of the 16S rDNA indicated that M21 is a member of the genus *Microbacterium*. The third strain, designated M30, is identified as one that degrades NNK. Molecular analysis of the 16S rDNA indicated that M30 was a bacterial strain belonging to the genus *Pseudomonas*.

Example 4—Use of M20 in the Bioremediation of Reconstituted Leaf

Figure 1B:
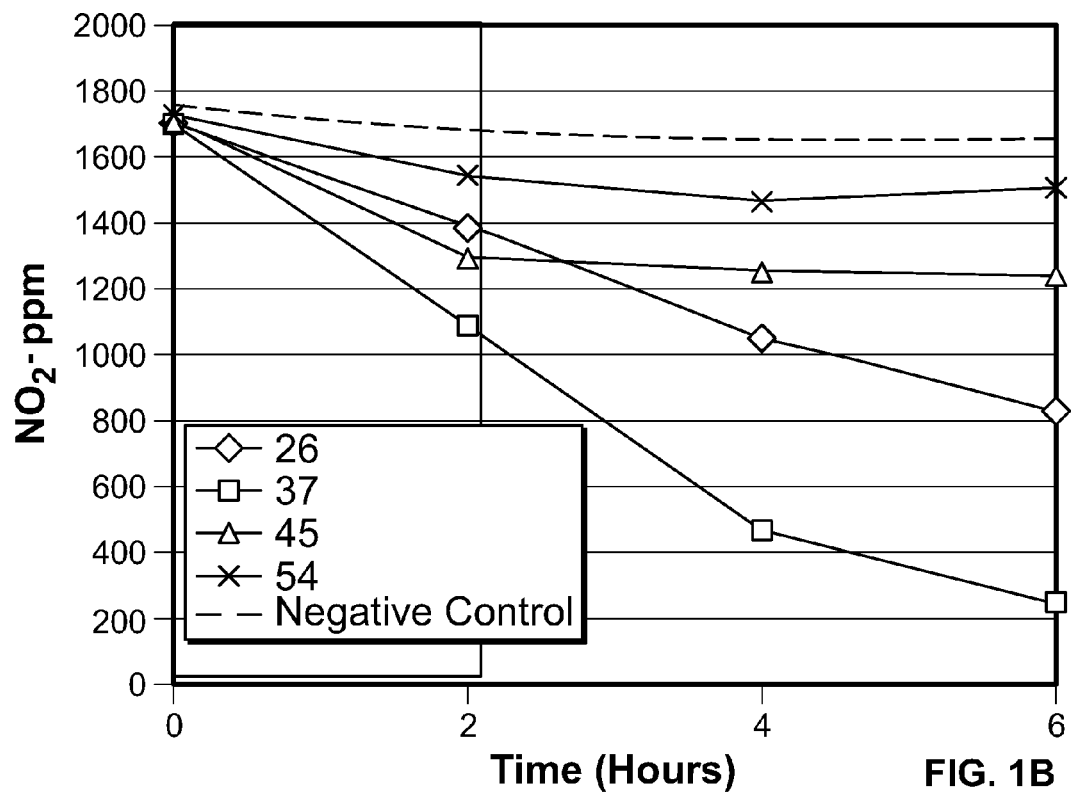

M20 was grown to mid-log phase, pelleted by centrifugation, and re-suspended in sterile saline. The bacteria were then added to the SEL. FIG. 1A is a graph that demonstrates the specific activity of the M20 bacteria toward NO2- in sterile SEL culture at temperatures ranging from 26 C to 54 C (i.e., 26 C, 37 C, 45 C, and 54 C), while FIG. 1B is a graph that demonstrates the specific activity of the M20 bacteria toward NO2- in native SEL culture at the same temperatures. To ensure that sufficient amounts of NO2- were present, 2000 ppm of excess NO2- was added to the SEL. The pH of the SEL was 7, and the culture was agitated at 225 RPM. Specific activity refers to the change in µmoles of NO2- per hour per $1 \times 10^{11}$ cells.

As can be seen in FIGS. 1A and 1B, $1 \times 10^{11}$ CFU/ml of M20 bacteria degraded µmolar amounts of NO2- within 1 hour, and these results were unaffected by the use of either sterile or native SEL. The specific activity of M20 bacteria under the conditions shown in FIGS. 1A and 1B are shown below in Table 1.

TABLE 1

Specific Activity of M20

| Temperature | Sterile* | Native* |
|---|---|---|
| 54 C. | 2.20 | 2.05 |
| 45 C. | 9.32 | 7.43 |
| 37 C. | 8.08 | 8.26 |
| 26 C. | 4.02 | 5.01 |

Figure 2A:
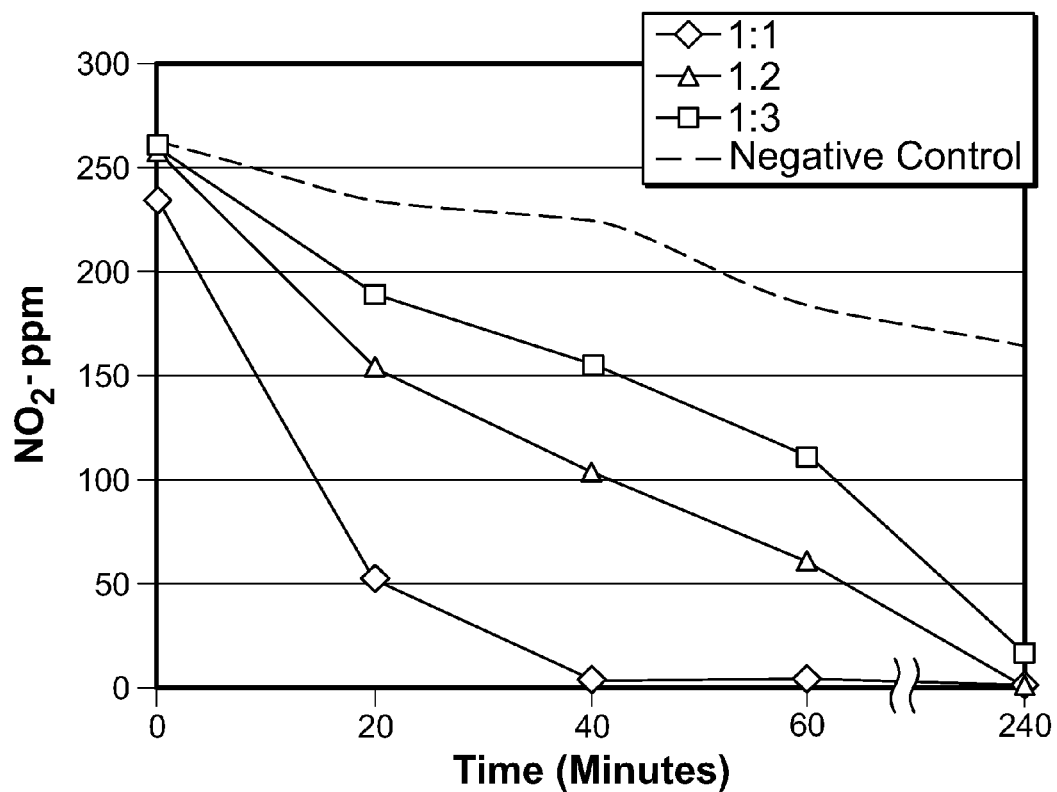
FIG. 2 are graphs showing the effects of inoculum levels in native SEL with (FIG. 2A) and without (FIG. 2B) added NO2-.
Figure 2B:
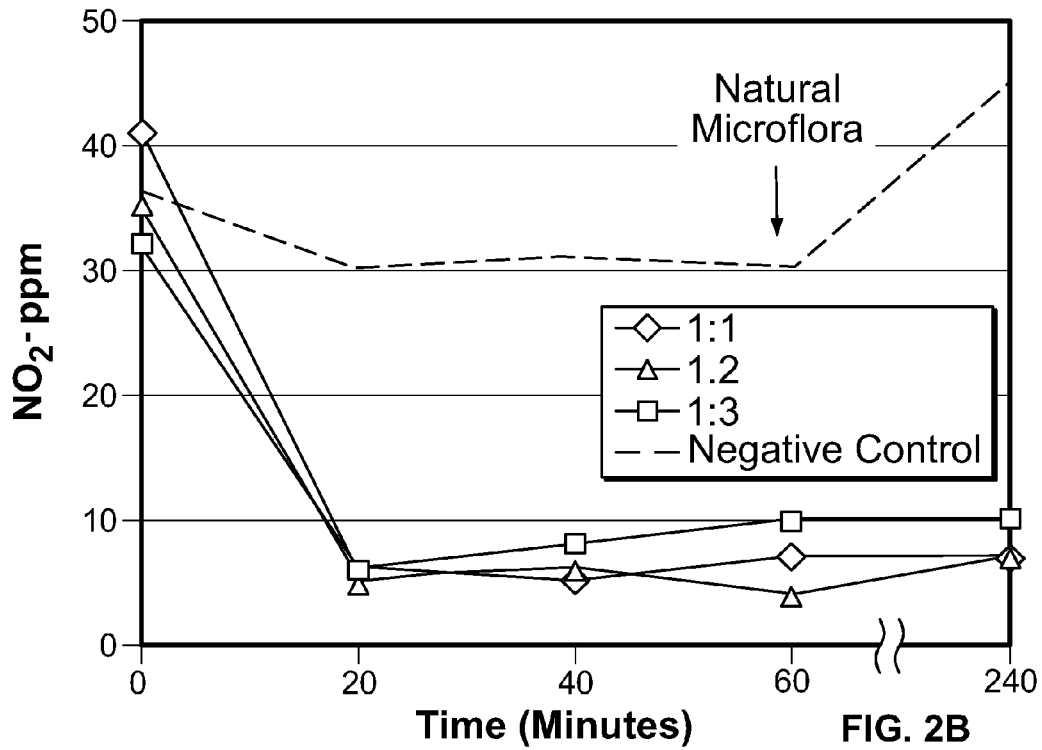

To determine how the concentration of M20 microorganisms in the SEL affected nitrite degradation, M20 was inoculated into SEL (pH 7) at a 1:1 M20:SEL ratio, a 1:2 M20:SEL ratio, or a 1:3 M20:SEL ratio. The culture was incubated at 45 C with agitation at 225 RPM and grown in the presence of 200 ppm added NO2- (FIG. 2A) or with no added NO2- (FIG. 2B). The results shown in FIG. 2 also is produced below in Table 2, which demonstrates that the NO2- was efficiently degraded at all of the concentrations of M20 used.

TABLE 2

Effects of Varying Amounts of Bacteria

| Ratio of M20:SEL | % Reduction after 60 min (w/added NO2—) | % Reduction after 60 min (w/out added NO2—) |
|---|---|---|
| 1:1 | 98 | 83 |
| 1:2 | 76 | 89 |
| 1:3 | 57 | 68 |

Figure 3A:
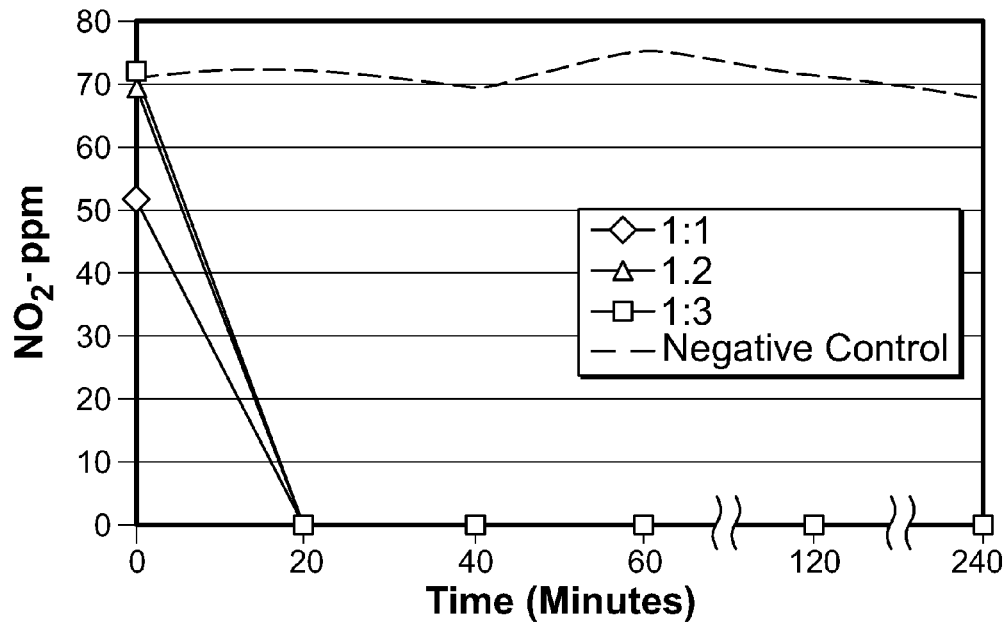
FIG. 3 are graphs showing that reduction of nitrite in the presence of M20 at a higher (FIG. 3A) or lower (FIG. 3B) shaking speed.
Figure 3B:
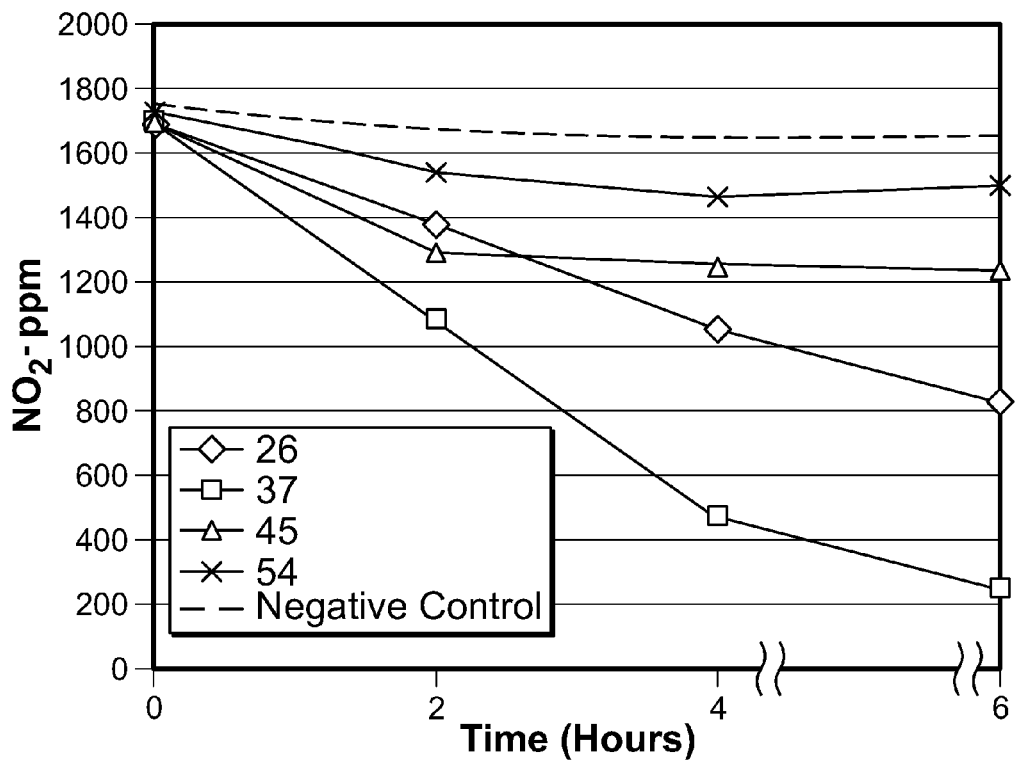

FIG. 3 shows that reduction of native nitrite (i.e., not added) in the presence of M20 proceeds at a fast rate. As shown in FIG. 3, NO2- was essentially eliminated (e.g., about 100% reduction) within about 20 minutes under standard conditions (e.g., a pH of 7 and a temperature of 45 C). The rapid degradation was observed whether the culture (300 ml SEL) was agitated at 225 RPM (FIG. 3A) or 67 RPM (FIG. 3B).

Example 5—Laboratory and Commercial Scale-Up

Figure 4A:
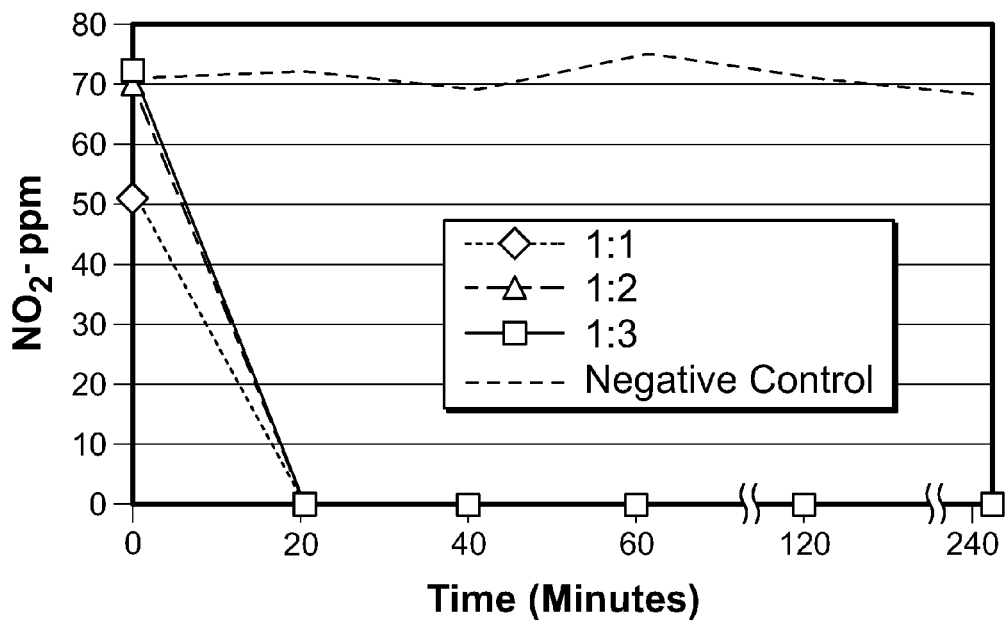
FIG. 4A is a 100-fold scale-up.
Figure 4B:
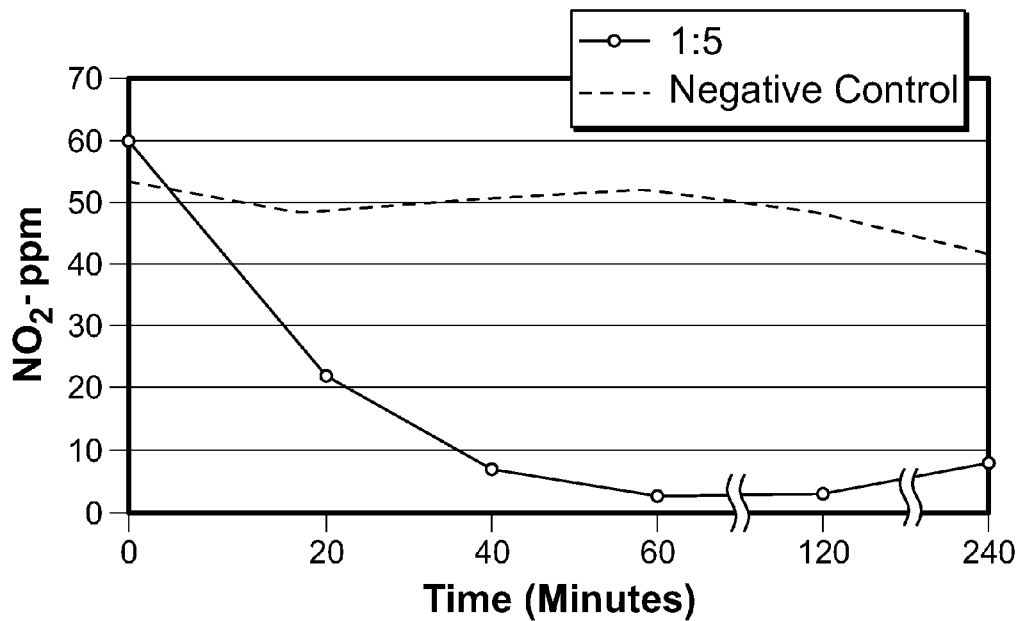
FIG. 4B is a 1,000-fold scale-up.
Figure 4C:
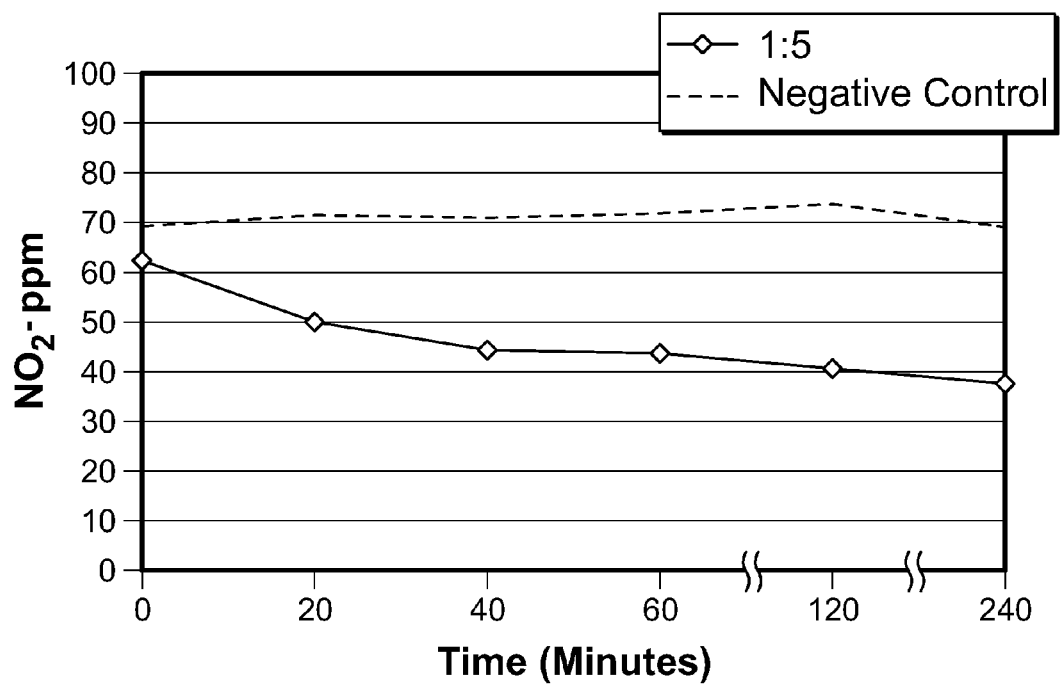
FIG. 4C is a 10,000-fold scale-up.

To ensure that the methods described herein can be repeated at a commercial level, the methods were scaled-up. FIG. 4A shows the results of an experiment in 300 ml SEL (with no added NO2-) at a pH of 7 and a temperature of 45 C. M20 bacteria were inoculated into SEL at the indicated ratios (1:1, 1:2, and 1:3), and the culture agitated at 225 RPM. As shown in the graph, a 100% reduction in NO2- was observed within about 20 minutes. FIG. 4B shows the results of an experiment in 3 L SEL (with no added NO2-) at a pH of 7 and a temperature of 45 C. M20 bacteria were inoculated into SEL at a ratio of 1:5, and the culture was agitated at 17 RPM. As shown in the graph, NO2- was reduced by about 95% within about an hour. FIG. 4C shows the results of an experiment in 30 L SEL (with 60 ppm NO2- added) at a pH of 7 and a temperature of 45 C. M20 bacteria were inoculated into the SEL at a ratio of 1:5, and the culture was agitated at 17 RPM. As shown in the graph, NO2- was reduced by about 20 ppm within the first hour.

Following the laboratory scale-up experiments, a commercial-pilot experiment was performed using over 900 L of SEL. M20 was grown to mid-log phase, concentrated by filtration, and re-suspended in sterile saline. M20 was inoculated at a 1:3 ratio of M20:SEL. The SEL was treated for 4 hours with slow agitation at 37 C, pH 5.4. Sterile saline was inoculated into the SEL at a 1:3 ratio of saline:SEL for the control.

Figure 7:
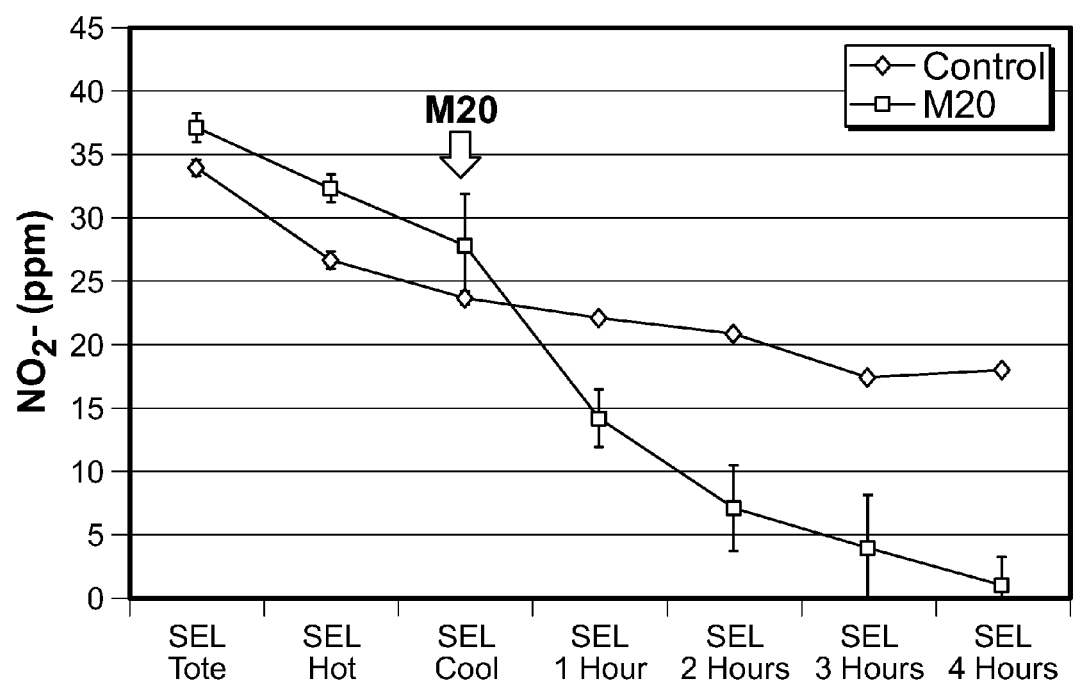
FIG. 7 is a graph showing the degradation of nitrite by M20 over time.
Figure 8A:
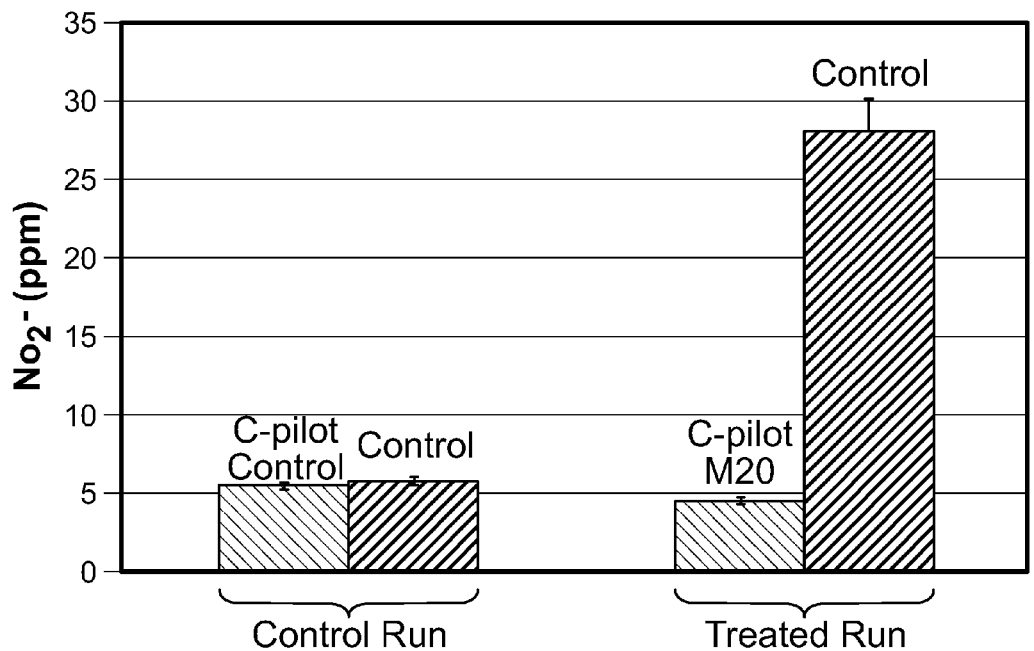
FIG. 8 is a graph showing the amount of nitrite (FIG. 8A) and TSNAs (FIG. 8B) in the final reconstituted sheet.
Figure 8B:
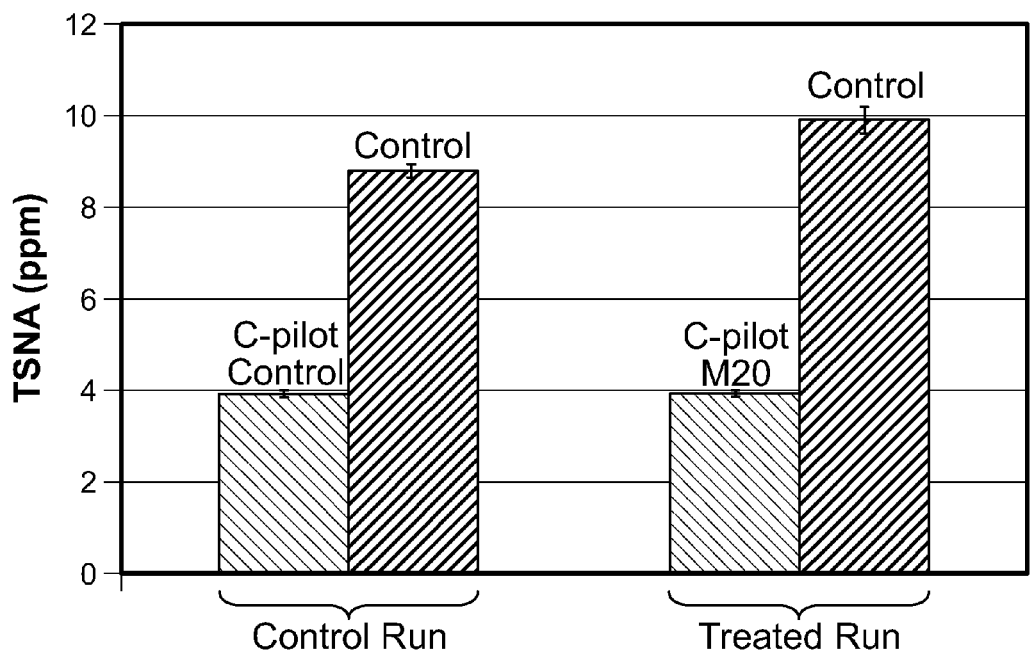
Figure 9A:
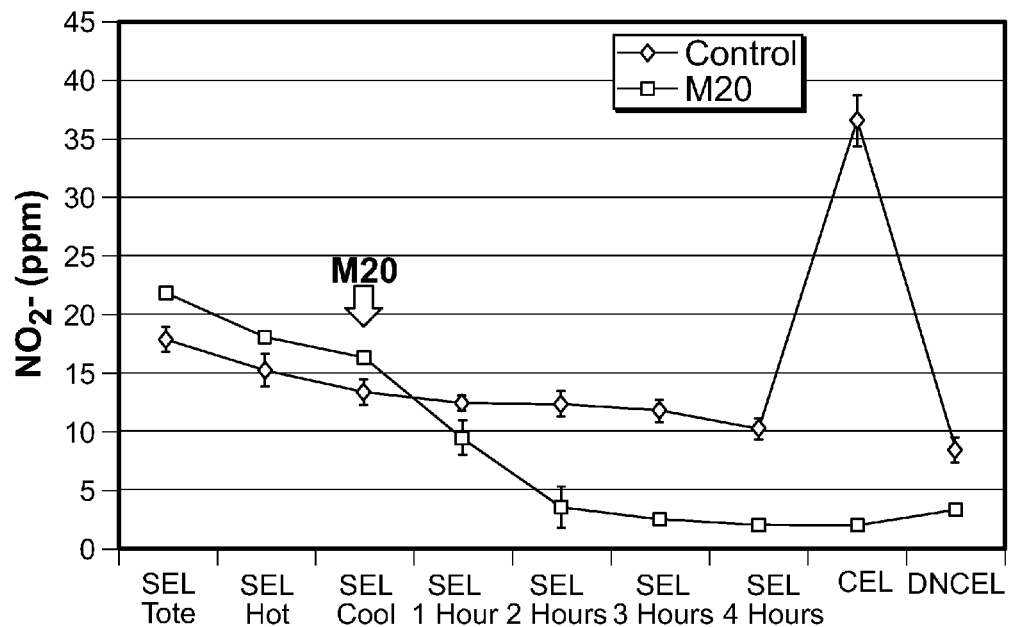
FIG. 9A is a graph showing the degradation of nitrite by M20 over time and FIG. 9B is a graph showing the amount of TSNAs in the CEL and the DNCEL following treatment of the SEL with M20.
Figure 9B:
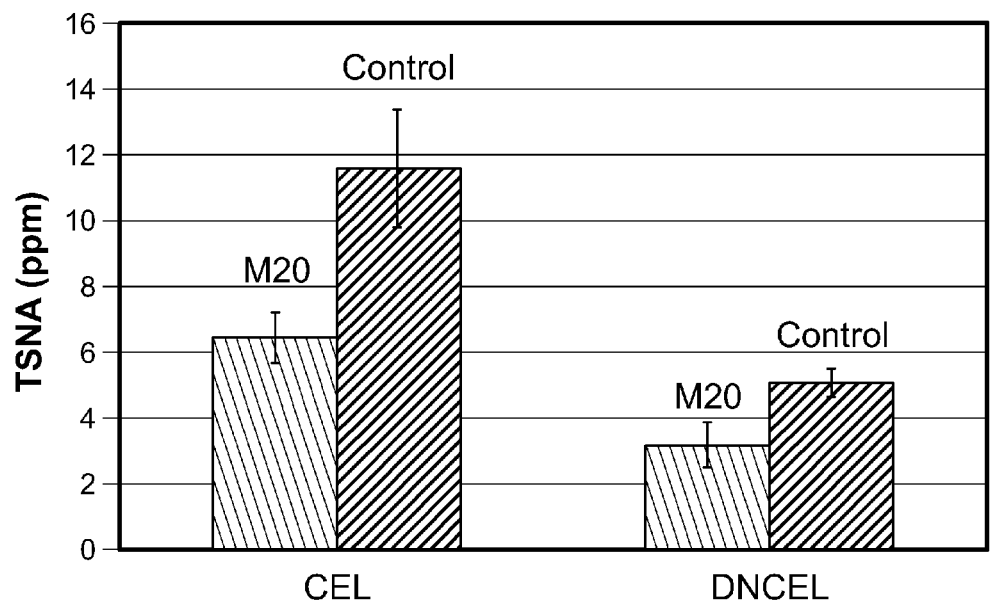
Figure 10A:
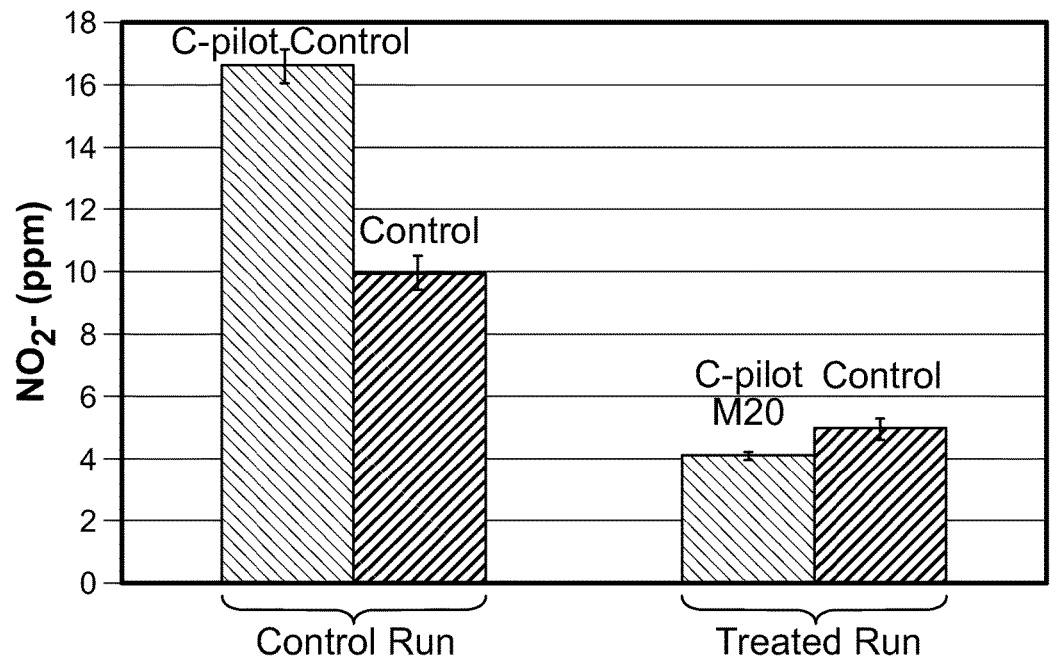
FIG. 10 are graphs showing the amount of nitrite (FIG. 10A) and TSNAs (FIG. 10B) in the final reconstituted sheet.
Figure 10B:
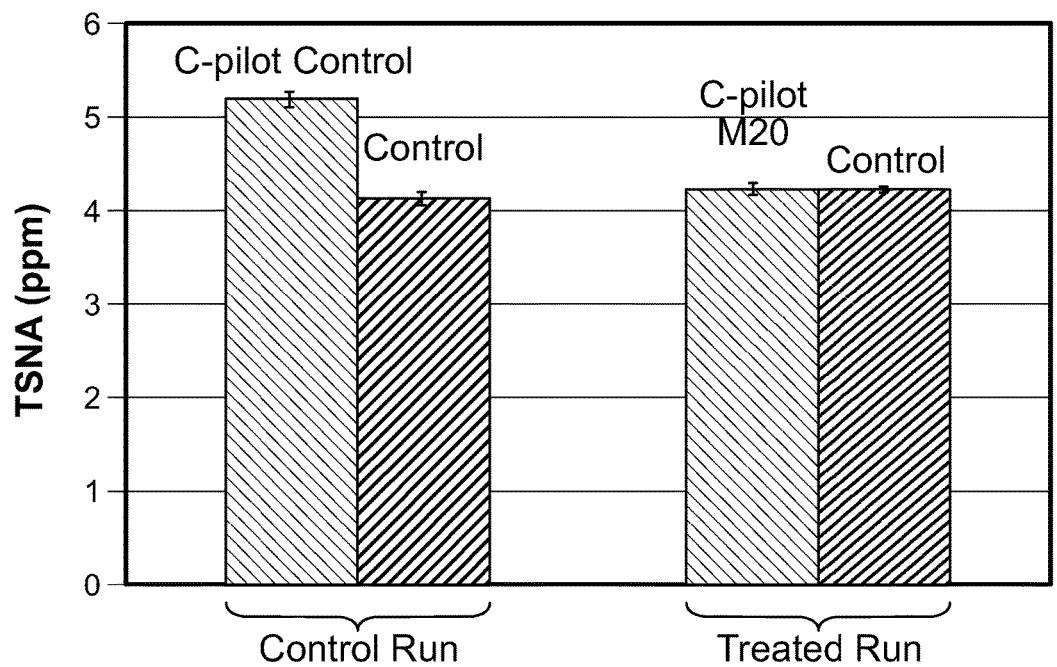

The first run showed a 95% reduction of nitrite in the SEL after 4 hours (FIG. 7). The first run showed little to no increase in the nitrite and TSNA in the final sheet compared to the control (FIGS. 8A and 8B). The second run showed an 88% reduction of nitrite in the SEL after 4 hours, which did not increase during the CEL step and only slightly increased during the DNCEL step (FIG. 9A). The TSNA levels in the CEL and DNCEL in the M20-treated batch in the second run showed a 44% and 37% decrease, respectively, in TSNA levels relative to the control (FIG. 9B). The second run showed a 75% reduction in nitrite in the final sheet (FIG. 10A) and a 19% reduction in TSNA in the final sheet (FIG. 10B).

Example 6—TSNA-Reducing Bacterial Strains and the Reduction of TSNAs in Tobacco Stems Bacterial strains designated A4M and M21 were identified as capable of degrading TSNAs. Using 16S rDNA sequencing, bacterial strain A4M was determined to be a mixture of *Arthrobacter* and *Microbacterium* spp., while bacterial strain M21 was determined to be from the *Microbacterium* genus.

Figure 5A:
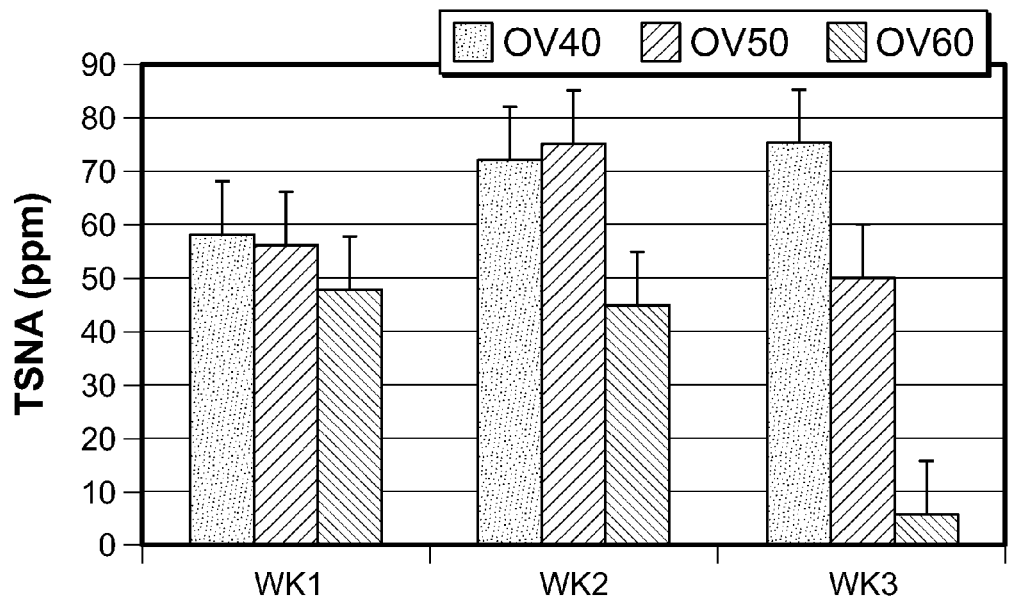
FIG. 5A is a graph showing TSNA concentration in tobacco stems incubated with bacterial isolate A4M.
Figure 5B:
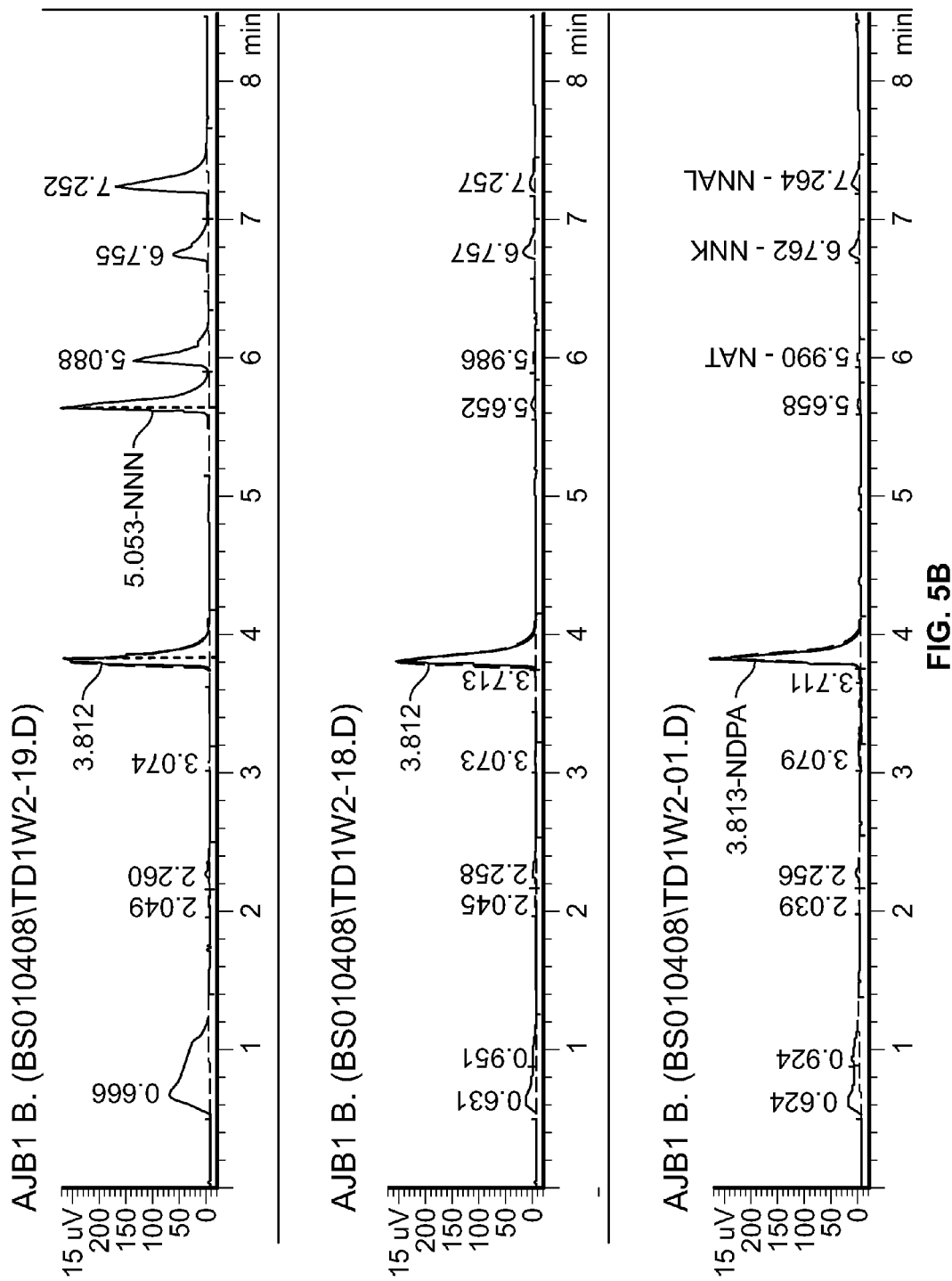
FIG. 5B is a gas chromatogram of TSNA content in sterilized tobacco stems (top chromatogram), tobacco stems incubated with bacterial isolate A4M (middle chromatogram), and tobacco stems incubated with bacterial isolate M21 (lower chromatogram). NNN, N'-nitrosonornicotine; NAT, N'-nitrosoanatabine; NNK, 4-(methylnitrosoamino)-1-(3-pyridyl)-1-butanone; NNAL, 4-(methylnitrosoamino)-1-(3-pyridyl)-1-butanol.

Bacterial isolates A4M and M21 were used to inoculate compositions that include tobacco stem having a moisture content of 40% to 60% by weight. The compositions were incubated in a drum with agitation for three weeks and the TSNA content was measured weekly. The results for A4M are shown in FIG. 5A. TSNA content was reduced from 70 ppm at the start to about 5 ppm at week 3 in the composition having a moisture content of 60%. FIG. 5B are the chromatographic results showing that NNN and NAT content was reduced in tobacco stems incubated with either A4M (middle) or M21 (bottom) as compared to a sterile control (top).

Example 7—Additional Nitrite- and/or TSNA-Reducing Bacterial Strains

Using the screening methods described herein, several additional nitrite- and/or TSNA-reducing bacterial strains were identified. For example, a bacterial strain designated 7M was identified based on its ability to degrade NNK and was determined to be a *Paracoccus* spp. A bacterial strain designated 7U was able to degrade NNK (and also nicotine) and was identified as *Arthrobacter nicotianae*. Several bacterial isolates, designated Colt 317, Colt 32, and M31, were able to degrade NNN, NAT, and NNK; all three strains were identified as *Microbacterium* spp.

Figure 6:
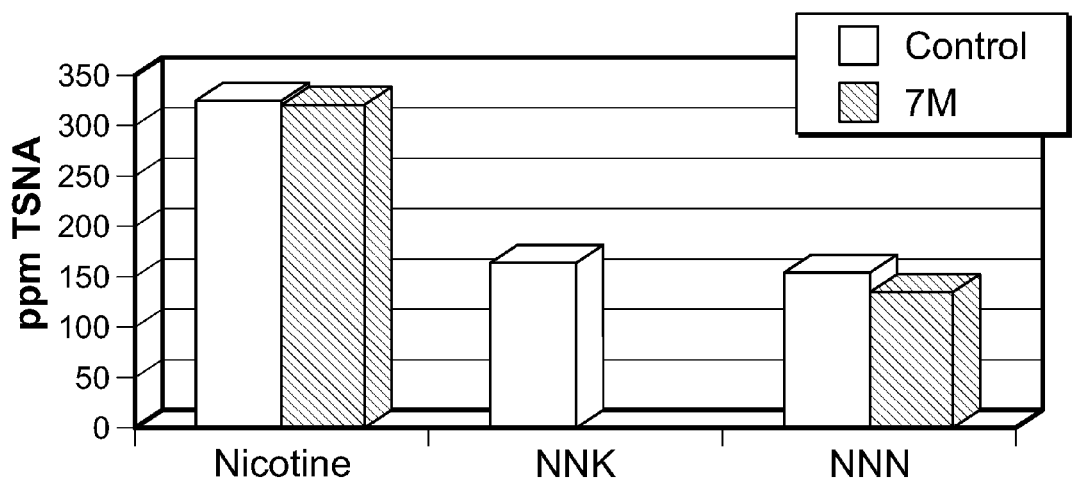
FIG. 6 is a graph showing the NNK-degrading activity of the 7M bacterial strain.

FIG. 6 is a graph showing the NNK-degrading activity of the bacterial strain designated 7M over 2 weeks in 10% TSB containing 150 ppm NNN and NNK and 300 ppm nicotine.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

DEPOSIT INFORMATION

A deposit of the proprietary *Myroides odoratus* M20 bacterial line disclosed above and recited in the appended claims have been made with American Type Culture Collection (ATCC®), 10801 University Boulevard, Manassas, Va. 20110, USA. The date of deposit for *Myroides odoratus* M20 was Jul. 20, 2018. The deposits of 25 vials of cells was taken from the same deposits maintained since prior to the filing date of this application. Upon issuance of a patent, all restrictions upon the deposits will be irrevocably removed, and the deposits are intended by applicant to meet all of the requirements of 37 C.F.R. § 1.801 1.809. ATCC® has issued the accession number: ATCC® Accession No. PTA-125147 for *Myroides odoratus* M20. This deposit will be maintained in the depository for a period of 30 years, or 5 years after the last request, or for the effective life of the patent, whichever is longer, and will be replaced as necessary during that period. Applicant does not waive any infringement of their rights granted under this patent or under the plant variety protection act (7 U.S.C. 2321 et seq.).

What is claimed is:

1. A method of reducing the amount of nitrites in strong extract liquor (SEL), comprising contacting SEL with the isolated bacterial strain *Myroides odoratus* M20 (ATCC® Patent Deposit Designation PTA-125147) under conditions in which the amount of nitrite is reduced in the SEL, thereby producing a reduced-nitrite SEL, wherein the bacterial strain comprises the 16S rDNA sequence having the sequence shown in SEQ ID NO: 1.

2. The method of claim 1, wherein the amount of nitrite in the SEL is reduced by at least 50%, compared to the amount of nitrite in the SEL prior to the contacting step.

3. The method of claim 1, wherein the amount of nitrite in the SEL is reduced by at least 75%, compared to the amount of nitrite in the SEL prior to the contacting step.

4. The method of claim 1, wherein the SEL is contacted with the isolated bacterial strain at a temperature of 26° C. to 37° C.

5. The method of claim 1, wherein the SEL is contacted with the isolated bacterial strain at a temperature of 37° C.

6. The method of claim 1, wherein the SEL is contacted with the isolated bacterial strain at a pH of 7.

7. The method of claim 1, wherein the SEL is contacted with the isolated bacterial strain for less than 2 hours.

8. The method of claim 1, wherein the SEL is contacted with the isolated bacterial strain for less than 10 hours.

9. The method of claim 1, wherein the SEL is contacted with the isolated bacterial strain for less than 24 hours.

10. The method of claim 1, wherein the SEL is contacted a second time with the isolated bacterial strain.

11. The method of claim 1, further comprising processing the SEL to produce concentrated extract liquor (CEL).

12. The method of claim 1, wherein the amount of nitrite in the SEL is reduced by at least 75%, compared to the amount of nitrite in the SEL prior to the contacting step.

13. The method of claim 1, wherein the amount of nitrite in the SEL is reduced by at least 95%, compared to the amount of nitrite in the SEL prior to the contacting step.

14. The method of claim 1, wherein the SEL is contacted with the isolated bacterial strain for less than 1 hour.

* * * * *

SEQUENCE LISTING

```
<160> NUMBER OF SEQ ID NOS: 1

<210> SEQ ID NO 1
<211> LENGTH: 1481
<212> TYPE: DNA
<213> ORGANISM: Myroides spp.

<400> SEQUENCE: 1
agagtttgat cctggctcag gatgaacgct agcggcaggc ctaacacatg caagtcgagg      60
ggtatagaga gcttgctttc tagagaccgg cggatgggtg agtaacgcgt atgcaaccta     120
ccttttacag gggaatagcc cggagaaatt cggattaatg ctccatggtt tatatgaatg     180
gcatcattta tataataaag atttatcggt aaaagatggg catgcgtatc attagctagt     240
tggtgtggta acggcatacc aaggcgacga tgattagggg tcctgagagg gagatccccc     300
acactggtac tgagacacgg accagactcc tacgggaggc agcagtgagg aatattggtc     360
aatggaggca actctgaacc agccatgccg cgtgcaggat gacggtccta tggattgtaa     420
actgcttttg tacgggaaga aatgtaatta cgtgtaatta tttgacggta ccgtaagaat     480
aaggatcggc taactccgtg ccagcagccg cggtaatacg gaggatccga gcgttatccg     540
gaattattgg gtttaaaggg ttcgtaggcg gtttagtaag tcagtggtga aatcttatag     600
cttaactata aaattgccgt tgatactgct agacttgaat agtatggaag taattagaat     660
atgtagtgta gcggtgaaat gcttagatat tacatggaat accaattgcg aaggcagatt     720
actacgtact tattgacgct gatgaacgaa agcgtgggta gcgaacagga ttagataccc     780
tggtagtcca cgccgtaaac gatggatact agctgttcgg ttttcggact gagtggctaa     840
gcgaaagtga taagtatcca cctggggagt acgttcgcaa gaatgaaact caaaggaatt     900 gacggggcc cgcacaagcg gtggagcatg tggtttaatt cgatgatacg cgaggaacct     960
taccaaggct taaatgtaga ttgacaggtt tagagataga cttttcttcg gacaatttac    1020
aaggtgctgc atggttgtcg tcagctcgtg ccgtgaggtg tcaggttaag tcctataacg    1080
agcgcaaccc ctattgttag ttgccagcgg gtcatgccgg gaactctaac aagactgccg    1140
gtgcaaaccg tgaggaaggt ggggatgacg tcaaatcatc acggcccttta cgtcttgggc    1200 tacacacgtg ctacaatggc cagtacagaa agcagctacc aggcaactgg atgcgaatct    1260
caaaaactgg tctcagttcg gattggagtc tgcaactcga ctccatgaag ctggaatcgc    1320
```

```
tagtaatcgg atatcagcca tgatccggtg aatacgttcc cgggccttgt acacaccgcc    1380
cgtcaagcca tggaagctgg gggtacctga agtcggtcgc cgcaaggagc tgcctagggt    1440
aaaactggta actagggcta agtcgtaaca aggtagccgt a                       1481
```